United States Patent
Berrier (10) Patent No.: US 7,433,730 B1
(45) Date of Patent: Oct. 7, 2008

(54) SYSTEMS AND METHODS FOR RECONSTRUCTING INFORMATION USING A DUNCAN AND HORN FORMULATION OF THE KALMAN FILTER FOR REGULARIZATION

(76) Inventor: Keith L. Berrier, 1238 Pondview La., White Bear Lake, MN (US) 55110

( * ) Notice: Subject to any disclaimer, the term of this patent is extended or adjusted under 35 U.S.C. 154(b) by 721 days.

(21) Appl. No.: 10/799,560

(22) Filed: Mar. 11, 2004

Related U.S. Application Data (60) Provisional application No. 60/454,204, filed on Mar. 11, 2003.

(51) Int. Cl.
*A61B 5/04* (2006.01)
(52) U.S. Cl. ...................................... 600/509
(58) Field of Classification Search ................. 600/508, 600/509, 510
See application file for complete search history.

(56) References Cited

U.S. PATENT DOCUMENTS

| | | | |
|---|---|---|---|
| 6,214,019 B1 * | 4/2001 | Manwaring et al. | 606/130 |
| 6,939,309 B1 * | 9/2005 | Beatty et al. | 600/508 |

OTHER PUBLICATIONS

D. Joly, Y. Goussard, and P. Savard, "Time-recursive solution to the inverse problem of electrocardiology: A Model-based approach," in Proc. 15th Ann. Int. Conf. IEEE EMBS, San Diego, CA, 1993, pp. 767-768.*
D. B. Duncan and S. D. Horn, "Linear dynamic recursive estimation from the viewpoint of regression analysis," J. Amer. Statist. Assoc., vol. 67, pp. 815-821, 1972.*
J. El-Jakl, F. Champagnat, and Y. Goussard, "Time-space regularization of the inverse problem of electrocardiography," in Proc. 17th Ann. Int. Conf. IEEE EMBS, Montréal, QC, Canada, 1995, pp. 213-214.*
H. S. Oster and Y. Rudy, "The use of temporal information in the regularization of the inverse problem of electrocardiography," IEEE Trans. Biomed. Eng., vol. 39, pp. 65-75, Jan. 1992.*
Berrier, Keith L., Sorensen, Danny C., Khoury, Dirar S. Solving the Inverse Problem of Electrocardiocardiography Using a Duncan and Horn Formulation of the Kalman Filter. Submitted IEEE Transactions on Biomedical Engineering. Feb. 21, 2003.*
Berrier, Keith L., Soresen, Danny C., Khoury, Dirar S. TR02-17: Solving the Inverse Problem of Electrocardiography Using a Duncan and Horn Formulation of the Kalman Filter. CAAM Technical Reports 2002, Dec. 2002. Found online at www.caam.rice.edu/caam/trs/tr02.html.*

* cited by examiner

*Primary Examiner*—George R Evanisko
*Assistant Examiner*—Amanda Patton
(74) *Attorney, Agent, or Firm*—Law Offices of Mark L. Berrier (57) ABSTRACT

Systems and methods for generating regularized solutions for inverse problems, where the regularization is performed using the Duncan-Horn formulation of a Kalman filter. The various alternative embodiments of the invention are applicable to many different types of inverse problems. In one electrocardiography implementation, electrical potentials are measured within a chamber of the heart and these measurements are processed to generate a mapping of the electrical activity at the interior surface of the heart chamber (these potentials at the heart s surface resulted in the potentials that were measured in the heart chamber). The generation of the mapping of the potentials at the heart s surface is regularized by using a Duncan-Horn formulation of a Kalman filter. The regularization may be based upon multiple steps in time, and the number of time steps may be selectable.

20 Claims, 5 Drawing Sheets

Fig. 5

SYSTEMS AND METHODS FOR RECONSTRUCTING INFORMATION USING A DUNCAN AND HORN FORMULATION OF THE KALMAN FILTER FOR REGULARIZATION

RELATED APPLICATIONS

The present application claims priority to U.S. Provisional Patent Application Ser. No. 60/454,204, filed Mar. 11, 2003 by Keith L. Berrier, entitled Improving the Electrocardiographic Inverse Solution by Kalman Filtering, which is hereby incorporated by reference in its entirety.

BACKGROUND

1. Field of the Invention

The present invention relates generally to the regularized solution of ill-conditioned problems and more particularly to ill-posed inverse problems, such as those found in the field of electrocardiography. An exemplary problem is the generation of a mapping of electrical potentials at the surface of the heart, based on measured potentials at positions that are not in contact with the heart surface.

2. Related Art

Every year in the United States alone, more than 200,000 patients die suddenly, due primarily to specific heart rhythm disorders that are caused by abnormal, rapid beats. Cardiac arrhythmia is one of the most common disorders in clinical practice. Current drug therapy for these irregular heart rhythms is often ineffective and, at times, can further complicate the rhythm abnormalities (including increased mortality). (For example, Pharmacologic therapy is generally not effective in the management of tachyarrhythmias.Super]) Radiofrequency ablation, a relatively new, minimally invasive, non-drug therapy has been shown to be relatively safe and effective in treating selected rhythm disorders; catheters inside the heart are used to deliver a energy to abnormal regions abolishing the cause of irregular beats. However, ablation of rhythm abnormalities that are brief, chaotic or hemodynamically unstable can be difficult given the limitations of the tools that are available to pinpoint the cause of these irregular beats. Radiofrequency (RF) catheter ablation has revolutionized the treatment of heart rhythm disorders, especially those for which the mechanisms are well understood, resulting in successful treatment. (For example, RF catheter ablation has revolutionized the treatment of supraventricular tachycardias, i.e., Wolff-Parkinson-White syndrome and atrioventricular nodal reentrant tachycardia, and atrial flutter.) However, for some disease the mechanism is not clear. For example, the mechanism is not clear in the cases of ventricular tachyarrythmia and atrial fibrillation. This is largely due to the inability to properly map the hearts activity using current mapping methods. To solve the problems associated with drug therapy and to advance alternative catheter-based therapies for eliminating heart rhythm abnormalities, improved methods are needed to map the electrical activity of the heart. The mapping of the heart s electrical activity can enable the physician to better localize the origin of irregular beats, to identify their causes, and to deliver the proper therapy, quickly. The solution of the discrete, ill-posed inverse problem of electrocardiography (the generating of a mapping of the hearts electrical activity based on measured potentials within the heart) is therefore needed.

The solution of the electrocardiographic inverse problem can aid in the diagnosis and treatment of disease manifesting itself in the hearts electrical activity. This must be done with care because of the ill-posed nature of the problem, as reflected in the ill-conditioning of the coefficient matrix (transfer function) that models the physical system. (Ill-conditioned, as used herein, refers to the fact that the system is near-numerically singular.) Inherent in the solution of the inverse problem using computer-based methods is the amplification of the measurement errors—often resulting in wildly varying solutions that are orders of magnitude greater than the heart is capable of producing. (For example, solutions in the millions of volts rather than in the tens of millivolts.) A simplified explanation of this problem is, for example, that the extraction of information from the measurements involves an amplification of parts of the signal to counter losses. In the process, any noise which is present is also amplified and, in fact, overwhelms the desired information. Several methods are currently used to mitigate the ill effects due to the poor conditioning and noisy measurements. Each method has its strengths and shortcomings. Some of these methods are mentioned later.

Typically, an instantaneous solution to the steady-state problem has been found with measurements made at a specific time. However, this problem has a temporal nature. Consider that a cardiac cell s activation stimulates neighboring cells and that this activation wave front travels outward through the myocardium (along the cardiac fibers). This temporal information is not part of the governing electrostatic equations (e.g., Maxwell s equations) and is not typically incorporated into solutions of inverse problems such as the electrocardiography inverse problem.

Just as there is a need to provide improved means for solving the inverse problem of electrocardiography described above, there is a need to provide improved means for solving other types of inverse problems. These problems may involve potential flow, heat transfer, groundwater flow, laminar fluid flow, etc. It is often the case that the desired information/signals cannot be observed or measured directly. Alternatively, making indirect measurements may be necessary in order to avoid some difficulty related to direct measurements. The indirect, measurable information/signals for these problems then require processing in order to extract/reconstruct the desired information/signals. In the electrocardiography example above, it is desired to map the electrical activity of the heart during disease related episodes when the heart s pumping action is compromised, but it is difficult to directly measure this electrical activity quickly (without grave risk to the patient). It is therefore desirable to be able to measure electrical potentials within one of the hearts chambers (thereby avoiding contact with the heart muscle itself) and to reconstruct the mapping of the heart s electrical activity from this information.

SUMMARY OF THE INVENTION

One or more of the problems outlined above may be solved by the various embodiments of the invention. Broadly speaking, the invention comprises systems and methods for generating regularized solutions for inverse problems, where the regularization is performed using the Duncan-Horn formulation of a Kalman filter. Although the description of the invention contained herein focuses primarily on an embodiment directed to an electrocardiography implementation, it should be noted that various alternative embodiments of the invention are possible, and these embodiments are applicable to many different types of inverse problems.

In one electrocardiography implementation, electrical potentials are measured within a chamber of the heart and these measurements are processed to generate a mapping of the electrical activity at the interior surface of the heart chamber (these potentials at the hearts surface resulted in the potentials that were measured in the heart chamber). The generation of the mapping of the potentials at the heart s surface is regularized by using a Duncan-Horn formulation of a Kalman filter. This implementation is intended to be illustrative of the possible embodiments, and should not be construed to limit the invention to electrocardiography implementations.

One embodiment comprises a method including receiving signals corresponding to a first parameter and performing an inversion of the received signals to generate a mapping of a second parameter, where the inversion is regularized by a Duncan and Horn formulation of a Kalman filter. In one embodiment, the regularization is based upon multiple steps in time, and the number of time steps may be selectable. In one embodiment, the first parameter corresponds to electrocardial potentials at a distance from a surface of the heart and the second parameter corresponds to electrocardial potentials at the surface of the heart. The potentials of the first parameter may be measured within or external to the heart, and the potentials of the second mapping may correspond to interior or exterior surfaces of the heart, respectively. The potentials may be measured by means of a multi-sensor probe that includes sensor elements such as simple electrodes, superconductive quantum interference devices (SQUIDs), magnetometers, electrometer amplifier based sensors, or the like. The sensors may be regularly or irregularly spaced, and the probe itself may have fixed or variable physical geometry. The results of the method may be improved by appropriate selection of parameters such as sensor element positioning on the probe, orientation and positioning of the probe (and sensor elements) with respect to the heart surface, and selection of points on the heart surface for which potential mappings will be generated.

Another embodiment comprises a system including a data processor that is coupled to a data input interface for receiving signals corresponding to a first parameter, and coupled to a data output interface for providing output signals corresponding to a second parameter. The data processor is configured to generate the output signals as a solution to an inverse problem. The solution of this inverse problem is regularized using a Duncan and Horn formulation of a Kalman filter. The data processor may be configured to perform the regularization based upon multiple steps in time, where the number of time steps may be selectable. In one embodiment, the system also includes a probe that is coupled to the data input interface. The probe is configured to measure the first parameter. In one embodiment, the system is configured to generate a mapping of heart surface potentials (the second parameter) based on measured potentials at a distance from the heart surface (the first parameter). The probe may measure potentials within or external to the heart, and the data processor may generate mappings of interior or exterior surfaces of the heart, respectively. The probe may include sensor elements such as simple electrodes, superconductive quantum interference devices (SQUIDs), magnetometers, electrometer amplifier based sensors, or the like to measure the potentials. The sensors may be regularly or irregularly spaced, and the probe may have fixed or variable physical geometry. The sensor element positioning on the probe, geometry of the probe and orientation and positioning of the probe may be varied to improve the generation of the potential mappings.

Numerous additional embodiments are also possible.

BRIEF DESCRIPTION OF THE DRAWINGS

Other objects and advantages of the invention may become apparent upon reading the following detailed description and upon reference to the accompanying drawings.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims.

DETAILED DESCRIPTION

One or more embodiments of the invention are described below. It should be noted that these and any other embodiments described below are exemplary and are intended to be illustrative of the invention rather than limiting.

As described herein, various embodiments of the invention comprise systems and methods for generating regularized solutions for inverse problems, where the regularization is performed using the Duncan and Horn formulation of a Kalman filter. These systems and methods may be used to solve many different types of inverse problems. While the various embodiments of the invention are applicable to many different types of inverse problems, the description of the invention contained herein focuses primarily on an embodiment directed to an electrocardiographical implementation in which electrical potentials are measured within a chamber of the heart and these measurements are processed to generate a mapping of the electrical activity at the interior surface of the heart chamber which resulted in the potentials that were measured in the heart chamber. This implementation is intended to be illustrative of the possible embodiments, and should not be construed to limit the invention to electrocardiography implementations.

Figure 1:
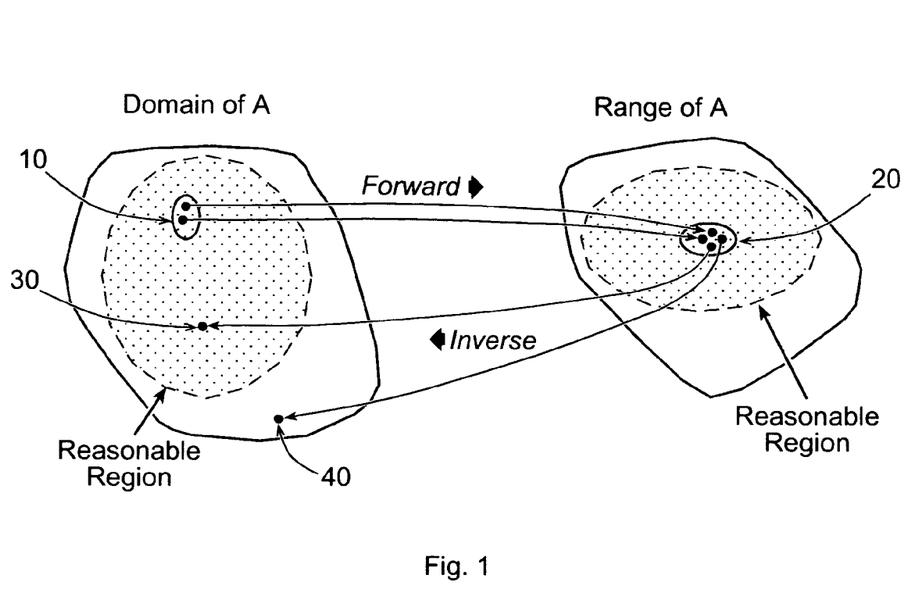
FIG. 1 is a diagram illustrating the domain and range of the transfer function associated with an inverse problem with one embodiment.

Referring to FIG. 1, a diagram illustrating an inverse problem is shown. A describes a relationship between two regions. In this figure, a first region (the Domain of A) contains the information that is desired. For example, the desired information may be the electrical potentials at a particular location. A second region (the Range of A) contains the information that is available to be measured. The shaded areas bounded by dashed lines represent values reasonable for a given physical system. A particular set of values in the Domain of A results in a corresponding set of values in the Range of A. In this figure, two small regions are identified by reference numbers 10 and 20. A forward correspondence from 10 to 20 is depicted. This forward relationship (forward problem) is stable and, when perturbed values of 10 are used in the forward problem, the result is values in 20 close to those resulting from the unperturbed values in 10. That is, perturbations to the input of the stable forward problem result in small changes to the forward solution.

Also shown is an correspondence from the Range of A to the Domain of A. The inverse problem may therefore be stated as identifying the set of values in Range of A and determining which of the many possible sets of values in Domain of A actually caused the set of values in Range of A to result. Ill-posed inverse problems present difficulties in determining the values of the Domain of A. Inappropriate (naive) techniques may result in meaningless solutions. In this figure, an inverse correspondence is depicted between two sets of values from the small region 20 in the Range of A to the two sets of values, 30 and 40, in the Domain of A. Even though the values from 20 are close to values from a forward solution and each other, the results of the inverse problem are far from the values in 10 and from each other. As is the case of 40, the solution may be wholly unreasonable. This illustrates that perturbations to the input of the ill-posed inverse problem resulted in large changes to the inverse solution.

Again, while in the forward problem small perturbations in the problem input (from the Domain of A) result in small changes in the solution of the forward problem, the converse may not be true and, in the ill-posed inverse problem, small perturbations in its input (from the Range of A) will result in large changes in its solution. The various embodiments of the present invention relate to means for improving the likelihood that the correct set of values in Domain of A (10, the set that actually caused set 20 to arise in Range of A) can be determined, or enabling the determination of a set of values that are closer to the correct set than would be possible using prior art methodologies.

Figure 2:
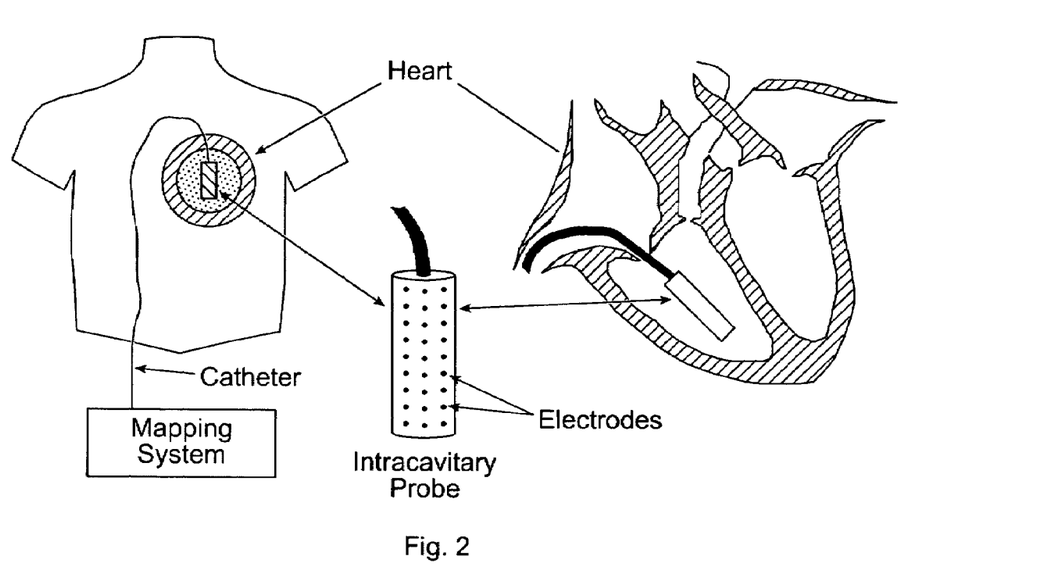
FIG. 2 is a diagram illustrating the positioning of an intracavitary, multielectrode probe within the heart in order to make measurements of electrical potentials within a chamber of the heart in accordance with one embodiment.

Referring to FIG. 2, a diagram illustrating the positioning of an intracavitary, multielectrode probe within the heart in accordance with one embodiment is shown. The left side of the figure depicts the approximate position of the probe and the heart within the chest cavity. The right side of the figure depicts in more detail the position of the probe within a chamber of the heart. The probe is depicted in the center of the figure. It should be noted that the illustrated arrangement pertains to endocardial mapping (within the heart) and that other electrocardiographic implementations could be epicardial (outside the heart).

The intracavitary probe includes a number of electrodes that are, in this embodiment, regularly spaced around the cylindrical surface of the probe. The probe is positioned in the heart chamber and is surrounded by the intracavitary blood. The electrodes are in contact with the blood, but not with the interior surface of the chamber of the heart. The electrodes are used to make measurements of the electrical potentials at multiple locations within the heart chamber. The regular spacing of the electrodes in this embodiment may simplify the processing of the data, but the electrode spacings may vary in other embodiments.

Figure 3:
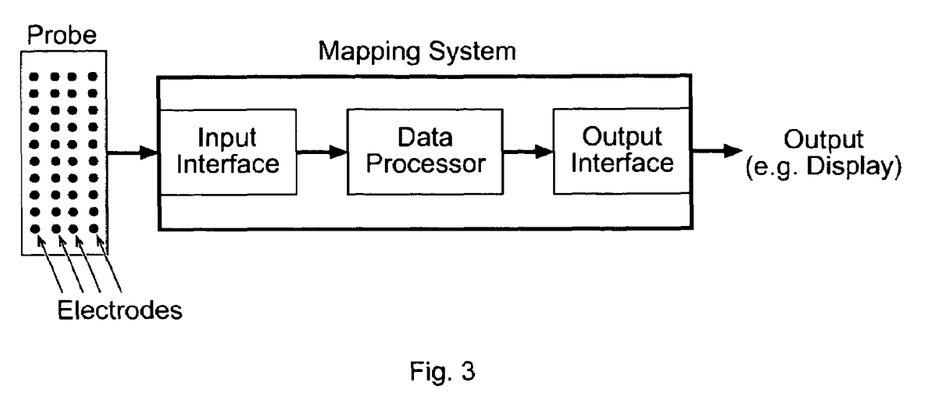
FIG. 3 is a diagram illustrating the components of a system for mapping the electrical potentials at a surface of the heart in accordance with one embodiment.

Referring to FIG. 3, a diagram illustrating the components of a system for mapping the electrical potentials at a surface of the heart in accordance with one embodiment is shown. In this embodiment, the system comprises a data processor coupled to an input interface and an output interface. The input interface is coupled to a multi-electrode probe to receive signals corresponding to the electrical potentials measured by the probe.

It should also be noted that probes in other embodiments may make use of elements other than simple electrodes to obtain the desired measurements. For example, the probe elements may comprise SQUIDs (Superconductive Quantum Interference Devices), magnetometers or electrometer amplifier based sensors.

The relative orientation and arrangement of the nodes used to describe the probe (electrodes) and the heart surfaces (the points at which the potentials are mapped) affects the basic properties of the transfer matrix. An appropriate choice of locations (positioning and orientation) of the probe, of the electrodes (e.g., staggering alternate rows of electrodes) and heart surface nodes (discretization) can improve the conditioning of the matrix by a few orders of magnitude.

The signals are processed by the data processor using a Duncan and Horn formulation of the Kalman filter to regularize the solution of the inverse problem (generation of a mapping of potentials on the heart s surface based on the measured potentials), as will be described in more detail below. The output of the data processor is provided at an output interface. The output data may be, for example, raw data or signals configured to drive a display device.

Figure 4:
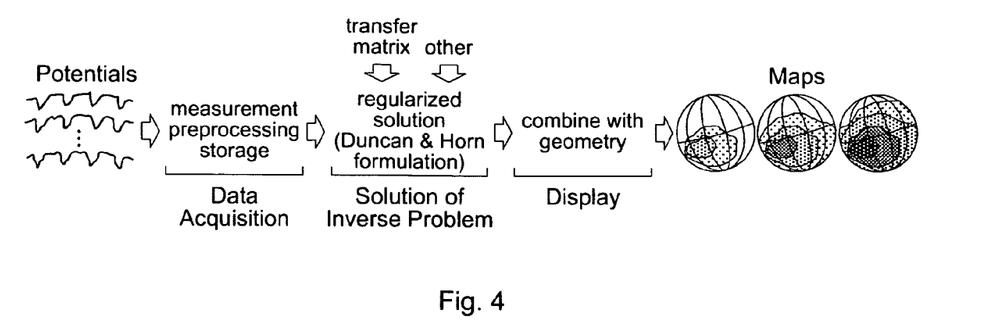
FIG. 4 is a flow diagram illustrating the electrocardiographic process in which electrical potentials measured within the heart chamber are used to generate a mapping of the electrical activity within the heart itself, in accordance with one embodiment.

Referring to FIG. 4, while the solution of the inverse problems described above may be broken down into an arbitrary number of stages, it is convenient for the purposes of this discussion to view the solution as being partitioned into three parts: acquiring measurements, performing the inversion, and displaying the results. This should not be construed to imply that the method cannot have other (e.g., adaptive/iterative) stages or elements. Performing the inversion involves regularization using a Duncan and Horn formulation of the Kalman filter. It is constructed using the transfer matrix/matrices and other information (including prediction matrices end error covariance estimates). This regularization makes use of temporal information to regularize the solution, or constrain it to not vary wildly from one point in time to the next.

FIG. 4 is a flow diagram illustrating the electrocardiographic process of one embodiment in which electrical potentials measured within the heart chamber are used to generate a mapping of the heart surface potentials induced by the electrical activity within the heart. Depicted in the figure are the acquisition, processing (inverse solution), and display of the potentials. In the process of FIG. 4 potentials are first measured. These potentials may be filtered to reduce or eliminate known noise (such as result from respiration), and may be stored before being passed into the inverse problem. The potentials are then processed to reconstruct the heart surface potentials. The solution of the inverse problem is performed using the Duncan and Horn formulation of the Kalman filter. The resulting potentials are then mapped to the heart geometry and displayed.

In the example of the inverse problem of electrocardiography, it is known that the electrical potentials in the heart muscle will vary over certain ranges, and in many instances will vary only slightly with incremental changes in time, so the regularization confines the solution of the inverse problem to these relatively small changes. Put another way, the regularization causes the solution to be well-behaved.

With respect to the electrocardiography inverse problem, it should be noted that prior art methods for solving the problem (i.e., for generating mappings of the heart surface potentials based on intracavitary measurements) typically did not take advantage of the temporal aspect of the problem. Instead, the temporal information was ignored. In one embodiment of the present invention, the mapping of the heart surface potentials is based upon a sliding window of temporal information. The manner in which the Duncan and Horn formulation of the Kalman filter makes use of the temporal information is described in detail below. As noted above, the inverse problem of electrocardiography is presented herein as an exemplary implementation, and is illustrative of the possible embodiments of the invention, rather than limiting.

Figure 5:
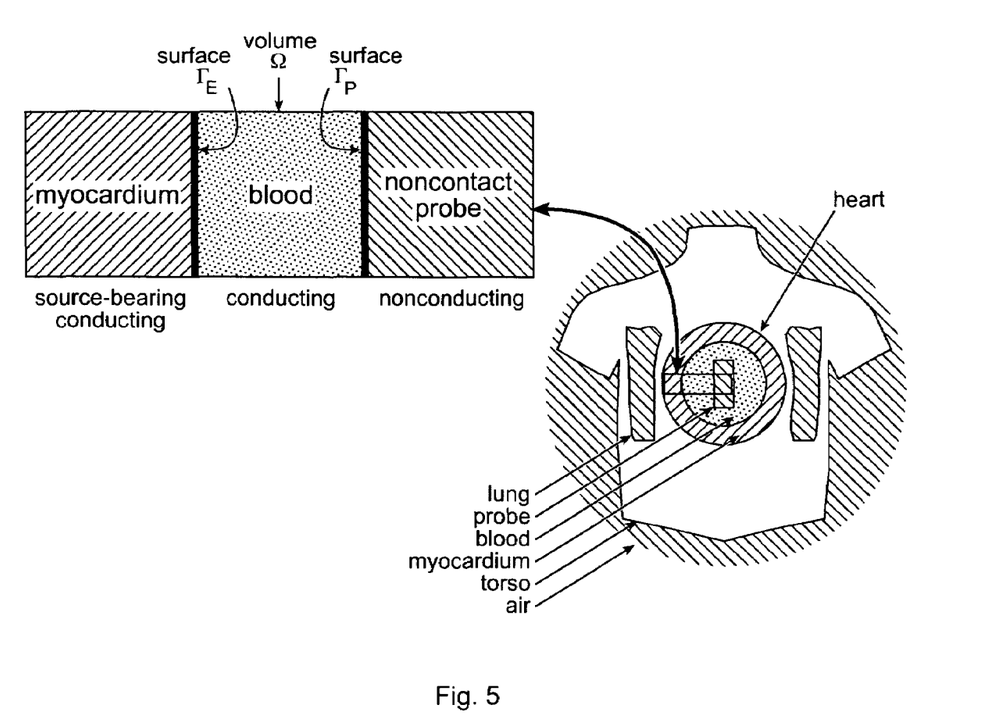
FIG. 5 is a diagram illustrating a schematic representation of the electrocardiographic inverse problem in accordance with one embodiment.

FIG. 5 is a diagram illustrating a schematic representation of the underlying physical problem addressed by the cardiographic embodiment described herein. On the right is a schematic of the heart within the torso. An intracavitary probe is positioned within a chamber of the heart. At the left side of the figure, is a diagram showing the relationship of the probe, the bounded volume conductor and the heart muscle (the myocardium).

For the endocardial problem the cavitary blood is the volume conductor $\Omega$, bounded by the interior surface source-bearing myocardium $\Gamma_E$ (endocardium) and the surface of the nonconducting probe $\Gamma_P$.

Referring again to FIG. 1, in the case of electrocardiography the Domain of A is the potentials at the surface of the heart and the Range of A is the potentials measured by an intracavitary probe, where A is the transfer matrix used to describe the relationship between the sets of potentials. The regions containing physiologically reasonable values are represented by the shaded areas with dashed boundaries. In the forward problem, points in the Domain of A (heart potentials) are mapped to points in the Range of A (probe potentials). In the inverse problem, points in the range are mapped to points in the domain.

As noted above, the forward problem of mapping points from the domain of A to the range of A is relatively straightforward and easy to solve. The inverse problem of mapping points from the Range of A (the probe potentials) to the domain of A (the heart) is much more difficult. This is due in great part to the amplification of noise that is included in the probe potential measurements. This noise may cause substantial variations. While a perturbation in the heart potentials may result in a small change in the resulting probe potentials, a small perturbation in the probe potentials can result in a large, even nonphysiologic change in the resulting heart potentials. The figure therefore shows some of the inverse mappings from the range of A extending into areas that are physiologically reasonable (the shaded areas) while others extend into areas that are not physiologically reasonable (the unshaded areas).

As pointed out above, the Duncan and Horn formulation of the Kalman filter enables the use of available temporal information and regularizes the solution of the inverse problem (in the electrocardiography case, the generation of the potential mapping at the surface of the heart). The Duncan and Horn formulation of the Kalman filter is not normally used to regularize inverse problems. Instead, regularization of inverse problems is typically limited to the use of spatial information. Accordingly, methods such as that of Tikhonov and Phillips are conventionally used in various forms to penalize/constrain a system s undesirable behavior or substituting a nearby problem in an attempt to improve the solutions generated for the corresponding inverse problem.

Kalman (and Bucy) previously described a recursive solution to the discrete-data linear filtering problem. These Kalman filters have often been employed in time-series analysis and are found in navigational systems (e.g. for use in combining the information from GPS, global positioning system, position and velocity data). Joly et al, and the closely related El-Jakl et al used the Kalman filter for the electrocardiographic inverse problem. They did not use the Duncan and Horn formulation but rather employed a simple recursive Kalman filter. This recursive filter requires expensive updates of the covariance matrices and suffers from the use of information losing matrix-transpose-matrix products. And, as experienced with navigation applications likely in need periodic restarts. In addition to avoiding the information loss and being less sensitive to user provided parameters, the Duncan and Horn formulation also produces additional smoothed states spanning a period of time.

The Duncan and Horn formulation of the Kalman filter is not viewed as a means for regularizing the solutions of inverse problems described herein. In other words, it is a tool that is not known to be useful in performing the required task. To use an analogy to carpentry tools, the Duncan and Horn formulation of the Kalman filter is roughly equivalent to a screwdriver and the solution of the inverse problem is roughly equivalent to driving a nail—it is known that one should use a hammer (i.e., known methods) to drive the nail instead of a screwdriver. The embodiments of the present invention, however, recognize that, while the Duncan and Horn formulation of the Kalman filter has not been used for this purpose in the past, it can be a useful tool in regularizing the solutions of inverse problems. To extend the carpentry tool analogy, the screwdriver is not intended to drive a nail, but it may be turned around and its handle used to pound in the nail.

Underlying Mathematical Model

The problem involves the volume conductor bounded by the probing electrodes and the surface of the source-bearing tissue (myocardium). See FIG. 5. The volume conductor $\Omega$ is composed of an electrically conductive media (e.g., the blood within the heart or the tissues within the torso) through which a current flows. The potential is designated $\phi(z)$ at a point in the conductor $z \in \Omega$ and the current flows in the direction $-\nabla\phi(z)$ (from high to low potential). The current is then $-\sigma(z)\nabla\phi(z)$ where $\sigma(z)$ is the conductivity of the media at the specified location. The net current (source) b is then given by the divergence $\nabla \cdot (-\sigma(z)\nabla\phi(z))$. This is known as Poisson s equation.

$$\nabla \cdot (-\sigma(z)\nabla\phi(z)) = b \qquad \text{EQ 1}$$

This reduces to Laplace s equation for the case when the volume conductor contains no sources.

$$\nabla^2 \phi(z) = 0 \quad z \in \Omega \qquad \text{EQ 2}$$

where, for example, the well-behaved volume conductor $\Omega$, consisting of the cavitary blood, is bounded by the probe $\Gamma_P$ and endocardial $\Gamma_E$ surfaces. The probe potentials are measured and the current density normal to the surface of the nonconducting probe is assumed zero.

$$u_P = \Phi(z_P) \qquad \text{EQ 3}$$

$$z_P \in \Gamma_P$$

$$q_P = \frac{\partial}{\partial n}\Phi(z_P) = 0$$

The boundary element method, for example, may be used to construct the linear system. The system consists of two influence matrices H and G, and two vectors that contain the potentials and their normal gradients on both the heart and probe surfaces. An appropriate partitioning and separation of variables result in $$Hu = Gq \rightarrow [H_E, -G_P]\begin{bmatrix} u_E \\ q_P \end{bmatrix} = [-H_P, G_E]\begin{bmatrix} u_P \\ q_P \end{bmatrix} \quad \text{EQ 4}$$

Consider $$[-H_P, G_E]^{-1}[H_E, -G_P]\begin{bmatrix} u_E \\ q_P \end{bmatrix} = \begin{bmatrix} A & M \\ C & N \end{bmatrix}\begin{bmatrix} u_E \\ q_P \end{bmatrix} = \begin{bmatrix} u_P \\ q_E \end{bmatrix} \quad \text{EQ 5}$$

Assuming that $q_P = 0$, then the potentials and current densities can be determined at the endocardial surface from $$Au_E = u_P \quad \text{EQ 6}$$

$$Cu_E = q_E \quad \text{EQ 7}$$

Equation 6 involves only the surface potentials and is the model commonly associated with the electrocardiographic inverse problem. The underlying ill-posedness is manifested in the ill-conditioning of the transfer matrix A. Calculating the endocardial potentials given the probe potentials is the inverse problem. In the unavoidable presence of measurement error, the inverse solutions are rendered useless, if unmoderated. To stabilize these solutions, regularizing methods are used.

Equation 7 contains the matrix $C \in R^{m \times n}$ that describes the relationship between the endocardial potentials and their normal gradients.

For the following discussion, let $x \equiv u_E$ and $b \equiv u_P$ with $X \equiv \{x_1, \ldots, x_d\}$ and $B \equiv \{b_1, \ldots, b_d\}$. The transfer function $A \in R^{m \times n}$ relates the endocardial potentials $X \in R^{n \times d}$ and probe potentials $B \in R^{m \times d}$ for the d times comprising the system $AX = B$.

Solution Techniques
Regularization

Regularization, stated simply, is a means of stabilizing the solution. It is necessary here because the solution does not depend continuously on the input (measurements) and the inputs contain errors. Regularization can include additional information to stabilize the solution. For example, the state nearly satisfying the linear system can be sought by minimizing the residual while penalizing the solution s bad behavior. This additional information is incorporated as the regularizing term of the following objective function.

$$\min_x (\|b - Ax\|^2 + \lambda F(x)) \quad \text{EQ 8}$$

The importance of the regularizing term is given by the regularization parameter (weight) $\lambda > 0$. The regularization term $\lambda F(x)$ can take many forms.

In the method of Tikhonov and Phillips the regularization term incorporates a regularization matrix D.

$$\min_x (\|Ax - b\|^2 + \lambda \|Dx\|^2) \quad \text{EQ 9}$$

The familiar solution is $$x_{Tik} = (A^T A + \lambda D^T D)^{-1} A^T b \quad \text{EQ 10}$$

When D is chosen such that $\text{rank}[A^T, D^T] = n$ and $\lambda$ is sufficiently large, the term to be inverted in EQ 10 is numerically nonsingular (well conditioned). The choices for D include measures of amplitude, smoothness, or proximity to an estimate. This approach is useful for the electrocardiographic inverse problem since the nonphysiologic behavior is manifested in wildly varying and unreasonably large solutions. The use of the n-order discrete derivative for D has led to the term n-order Tikhonov regularization. For the electrocardiographic inverse problem the identity is the dominant choice for D (zero-order Tikhonov), which limits the solution amplitude. Improvements have been observed using a regularization matrix other than the identity. For example, matrix C from EQ 7 (D=C) which is equivalent to constraining current density at the endocardial surface.

The method of Twomey uses an error with respect to an estimate as the regularizing term.

$$\min_x (\|Ax - b\|^2 + \lambda \|x - x_{est}\|^2) \quad \text{EQ 11}$$

$$x_{Twomey} = (A^T A + \lambda I)^{-1} (A^T b + \lambda x_{est}) \quad \text{EQ 12}$$

Oster and Rudy illustrated the use temporal information with Twomey regularization. The estimates of the potentials were calculated from measured potentials in the immediate vicinity of the current time. The estimates were formed from the truncated Taylor series (difference formulas). The estimates which were not forward-looking are $$x_{est}(t) = \begin{cases} x(t-1) \\ 2x(t-1) - x(t-2) \end{cases} \quad \text{EQ 13}$$

Other methods exist as well as the aforementioned.
Kalman Filter

The Kalman filter can take advantage of the temporal nature of the electrocardiographic inverse problem. Simply, a Kalman (Kalman-Bucy) filter uses a recursive scheme that first predicts, then corrects an estimate of the state (potentials) using a process model and a measurement model, respectively. Temporal information is not only incorporated by the predictor but carried by the error variance-covariance matrices as well. A simple formulation is presented to illustrate the predictor-corrector nature of the filter. An alternate scheme is then presented; the equations for the predictor and corrector are combined into a single linear system as described by Duncan and Horn and solved as a weighted least squares problem. This may then be solved by the usual means or a one such as the solution by Paige and Saunders.

The two major steps of the recursive Kalman filter predict and correct the endocardial potentials (state). Predictions are made for the endocardial potentials and error covariance (EQ 16). Updates are then made for the Kalman gain K, endocardial potentials x, and error covariance P (EQ 17). These process and measurement models comprise the (possibly time-varying) state-space model for the problem. In this typical Kalman filter the covariance matrices P are recursed making the filter a covariance filter. (The variance-covariance matrix is simply referred to as the covariance matrix.) The linear estimation (process) model of the predictor is $$x_k = G_k x_{k-1} + v_{xk} \quad \text{EQ 14}$$

incorporating information from spatiotemporal neighbors where the endocardial potentials at time $t_k$ are estimated from those at time $t_{k-1}$. The measurement model of the corrector is $$b_k = A_k x_k + \epsilon_{bk} \quad \text{EQ 15}$$

where the transfer function $A_k$ relates the surface potentials: the probe measurements $b_k$ and the endocardial potentials $x_k$ ($x_k^+$) at time $t_k$. The vectors $\epsilon_{xk}$ and $\epsilon_{bk}$ above are the errors and the corresponding $V_k$ and $W_k$ below are the estimates of the error variance-covariance matrices.

Predictor $$x_k^- = G_k x_{k-1}^+$$

$$P_k^- = G_k P_{k-1}^+ G_k^T + V_k \quad \text{EQ 16}$$

Corrector $$K_k = P_k^- A_k^T (A_k P_k^- A_k^T + W_k)^{-1}$$

$$x_k^+ = x_k^- + K_k(b_k - A_k x_k^-)$$

$$P_k^+ = (I - K_k A_6) P_k^- \quad \text{EQ 17}$$

The pre- and post-measurement values are indicated by the superscript minus (−) and plus (+), respectively.

The transfer matrix relating the probe and endocardial potentials is used as the measurement model but the underlying process is not well-defined and a definitive predictor is not available. Fortunately, one of the benefits of using the Kalman filter is that such an uncertain process model (predictor) can be used. A scalar multiple of the identity may be used for the process model $G_k$ (making the prediction proportional to the previous solution).

Duncan and Horn Formulation

Duncan and Horn describe an alternate formulation of the Kalman filter where the equations from the predictor and corrector are combined into a single linear system. A block is added for each additional point in time and the system solved as a weighted least squares problem using the standard deviation of the errors.

Duncan and Horn formulated the discrete problem such that the state estimates are the solutions to the sequence of weighted linear least squares problems (each comprising k sets of equations).

$$\min \nu F^{(k)} x^{(k)} - y^{(k)} \| \quad k = 1, 2, \ldots \quad \text{EQ 18}$$

where $F^{(k+1)}$ is $F^{(k)}$ with additional rows and columns, and the state and measurement vectors (x and y) gain a corresponding addition of rows. (An artifact of this formulation is that the resulting algorithm produces both the so-called filtered and possibly several smoothed states at each step, as described below. A separate smoother is not used.) This system is weighted with factors of the error covariance matrices. To construct this system consider the prediction and correction steps (beginning at some step 1) through time k.

$$\begin{aligned} x_1 &= x_{init} + \varepsilon_{x1} & b_1 &= A_1 x_1 + \varepsilon_{b1} \\ x_2 &= G_2 x_1 + \varepsilon_{x2} & b_2 &= A_2 x_2 + \varepsilon_{b2} \\ &\vdots & &\vdots \\ x_k &= G_k x_{k-1} + \varepsilon_{xk} & b_k &= A_k x_k + \varepsilon_{bk} \end{aligned} \quad \text{EQ 19}$$

These can be rewritten as an augmented system where the $x_{i|j}$ states are simultaneously determined at time i, each calculated using data from j−i+1 times.

$$\begin{bmatrix} -x_{init} \\ b_1 \\ 0 \\ b_2 \\ 0 \\ \vdots \\ 0 \\ b_k \end{bmatrix} = \begin{bmatrix} -I & & & & \\ A_1 & & & & \\ G_2 & -I & & & \\ & A_2 & & & \\ & G_3 & -I & & \\ & & \ddots & \ddots & \\ & & & G_k & -I \\ & & & & A_k \end{bmatrix} \begin{bmatrix} x_{1|k} \\ x_{2|k} \\ x_{3|k} \\ \vdots \\ x_{k|k} \end{bmatrix} + \begin{bmatrix} \varepsilon_{x1} \\ \varepsilon_{b1} \\ \varepsilon_{x2} \\ \varepsilon_{b2} \\ \varepsilon_{x3} \\ \vdots \\ \varepsilon_{xk} \\ \varepsilon_{bk} \end{bmatrix} \quad \text{EQ 20}$$

The error vectors are assumed to have zero mean with symmetric nonnegative definite covariance matrices. (E( ) denotes the expectation.)

$$E(\epsilon_{xk}) = 0, \; E(\epsilon_{bk}) = 0 \quad \text{EQ 21}$$

$$E(\epsilon_{xk} \epsilon_{sk}^T) = V_k = S_{xk} S_{sk}^T$$

$$E(\epsilon_{bk} \epsilon_{bk}^T) = W_k = S_{bk} S_{bk}^T \quad \text{EQ 22}$$

The errors are then equilibrated by premultiplying EQ 20 with the inverse of the square root of the covariance matrices.

$$\begin{bmatrix} -S_{x1}^{-1} x_{init} \\ S_{b1}^{-1} b_1 \\ 0 \\ S_{b2}^{-1} b_2 \\ 0 \\ \vdots \\ 0 \\ S_{bk}^{-1} b_k \end{bmatrix} = \begin{bmatrix} -S_{x1}^{-1} & & & & \\ S_{b1}^{-1} A_1 & & & & \\ S_{x2}^{-1} G_2 & -S_{x2}^{-1} & & & \\ & S_{b2}^{-1} A_2 & & & \\ & S_{x3}^{-1} G_3 & -S_{x3}^{-1} & & \\ & & \ddots & \ddots & \\ & & & S_{xk}^{-1} G_k & -S_{xk}^{-1} \\ & & & & S_{bk}^{-1} A_k \end{bmatrix} \begin{bmatrix} x_{1|k} \\ x_{2|k} \\ x_{3|k} \\ \vdots \\ x_{k|k} \end{bmatrix} + \quad \text{EQ 23}$$

$$\begin{bmatrix} S_{x1}^{-1} \varepsilon_{x1} \\ S_{b1}^{-1} \varepsilon_{b1} \\ S_{x2}^{-1} \varepsilon_{x2} \\ S_{b2}^{-1} \varepsilon_{b2} \\ S_{x3}^{-1} \varepsilon_{x3} \\ \vdots \\ S_{xk}^{-1} \varepsilon_{xk} \\ S_{bk}^{-1} \varepsilon_{bk} \end{bmatrix}$$

This is the weighted problem of EQ 18.

$$y^{(k)} = F^{(k)} x^{(k)} + \epsilon^{(k)} \quad \text{EQ 24}$$

where the superscript indicates the number of measurements (partitions). The least squares solution is $$x^{(k)} = \begin{bmatrix} x_{1|k} \\ x_{2|k} \\ x_{3|k} \\ \vdots \\ x_{k|k} \end{bmatrix} \cong \operatorname{argmin} \| F^{(k)} x^{(k)} - y^{(k)} \| \; k \in \{1, 2, \ldots\} \quad \text{EQ 25}$$

where the $i^{th}$ partition $x^{i|j}$ is the state (potentials) at time i calculated using data from j−i+1 times, (i=j)⇒ filtered, and (i<j) ⇒ smoothed. That is, the solution contains the smoothed states in addition to the filtered state. The system becomes larger with an increase in the number of retained, smoothed states. The first partition contains the most smoothed and the last contains the filtered. These states are simultaneously determined and the system can be truncated to the desired number of states (e.g., a sliding window of the desired size can be used).

Additional Solution Method

A simple solve may be performed. Also, Methods other than a simple solve may be used. Paige and Saunders describe the use of QR factorizations in the solution of the Duncan and Horn augmented system. The transfer matrix can be put into the more easily solved, upper triangular form.

$$(Fx = y) \rightarrow (Q^T F x = Q_y^T) \rightarrow \left( \begin{bmatrix} R \\ 0 \end{bmatrix} x = \begin{bmatrix} Q_1^T y \\ Q_2^T y \end{bmatrix} \right) \quad \text{EQ 26}$$

Use the following notation for EQ 23.

$$\begin{bmatrix} \overline{S_1} \\ \overline{A_1} \\ \overline{G_2} & \overline{S_2} \\ & \overline{A_2} \\ & \overline{G_3} & \overline{S_3} \\ & & \ddots & \ddots \\ & & & \overline{G_k} & \overline{S_k} \\ & & & & \overline{A_k} \end{bmatrix} \begin{bmatrix} x_{1|k} \\ x_{2|k} \\ x_{3|k} \\ \vdots \\ x_{k|k} \end{bmatrix} = \begin{bmatrix} \overline{y_{init}} \\ \overline{y_1} \\ 0 \\ \overline{y_2} \\ 0 \\ \vdots \\ 0 \\ \overline{y_k} \end{bmatrix} \quad \text{EQ 27}$$

The transformation of each block is $$Q^T \begin{bmatrix} \overline{R_j} & 0 \\ \overline{A_j} & 0 \\ \overline{G_{j+1}} & \overline{S_{j+1}} \end{bmatrix} = \begin{bmatrix} R_j & R_{j,j+1} \\ 0 & 0 \\ 0 & \overline{R}_{j+1} \end{bmatrix} \quad \text{EQ 28}$$

$$P^T \begin{bmatrix} R_j & R_{j,j+1} \\ 0 & 0 \\ 0 & \overline{R}_{j+1} \end{bmatrix} = \begin{bmatrix} R_j & R_{j,j+1} \\ 0 & \overline{R}_{j+1} \\ 0 & 0 \end{bmatrix} \quad \text{EQ 29}$$

$$Q^T = P^T \overline{Q}^T \quad \text{EQ 30}$$

Or, alternatively, the transformation is $$Q^T \begin{bmatrix} \overline{R_j} & 0 \\ \overline{G_{j+1}} & \overline{S_{j+1}} \\ 0 & \overline{A_{j+1}} \end{bmatrix} = \begin{bmatrix} R_j & R_{j,j+1} \\ 0 & \overline{R}_{j+1} \\ 0 & 0 \end{bmatrix} \quad \text{EQ 31}$$

The augmented system is then transformed $$\begin{bmatrix} R_1 & R_{1,2} \\ & R_2 & R_{2,3} \\ & & R_3 & \ddots \\ & & & \ddots & R_{k-2,k-1} \\ & & & & R_{k-1} & R_{k-1,k} \\ & & & & & \overline{R}_k \end{bmatrix} \begin{bmatrix} x_{1|k} \\ x_{2|k} \\ x_{3|k} \\ \vdots \\ x_{k-1|k} \\ x_{k|k} \end{bmatrix} = \begin{bmatrix} y_1 \\ y_2 \\ y_3 \\ \vdots \\ y_{k-1} \\ y_k \end{bmatrix} \quad \text{EQ 32}$$

With the addition of new measurements only the submatrix $\overline{R}_k$ is altered by the update of the factorization. When the transfer function A, predictor G, and error covariance estimates V and W remain constant, then further simplifications may be applied, eliminating the need for recurring factorizations, reducing storage requirements and allowing for a more efficient (sparse) solver.

The mathematical model described above illustrates the implementation of the Duncan and Horn formulation of the Kalman filter as implemented in embodiments of the present invention. These embodiments may thereby provide substantial benefits in the solution of inverse problems where measurement errors are inevitable and where these errors would otherwise render simple, unmoderated solutions useless (e.g., in the discrete ill-posed inverse problem of electrocardiography).

The embodiments of the invention employ, for the first time, a Duncan and Horn formulation of the Kalman filter to solve inverse problems such as the electrocardiographic inverse problem described above. Improvements can be illustrated in (for example) total relative error and average activation time error, and better representations (contour shape) of isopotential and isochrone maps compared to results derived from previously used spatial and temporal regularization methods. The Duncan and Horn formulation is superior to the typical recursive formulation, having eliminated the information-losing matrix-matrix transpose products. In addition, a method such as the Paige and Saunders technique (using a QR factorization) can improve this further. A separate issue is the determination of (adaptive) means to estimate (measurement) error covariances.

Those of skill in the art will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. The information and signals may be communicated between components of the disclosed systems using any suitable transport media, including wires, metallic traces, vias, optical fibers, and the like.

Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Those of skill in the art may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with general purpose processors, digital signal processors (DSPs) or other logic devices, application specific integrated circuits (ASICs), field programmable gate arrays (FPGAs), discrete gates or transistor logic, discrete hardware components, or any combination thereof designed to perform the functions described herein. A general purpose processor may be any conventional processor, controller, microcontroller, state machine or the like. A processor may also be implemented as a combination of computing devices, e.g., a combination of a DSP and a microprocessor, a plurality of microprocessors, one or more microprocessors in conjunction with a DSP core, or any other such configuration.

The steps of the methods or algorithms described in connection with the embodiments disclosed herein may be embodied directly in hardware, in software or firmware modules executed by a processor, or in a combination thereof. A software module may reside in RAM memory, flash memory, ROM memory, EPROM memory, EEPROM memory, registers, hard disk, a removable disk, a CD-ROM, or any other form of storage medium known in the art. An exemplary storage medium may be coupled to the processor such that the processor can read information from, and write information to, the storage medium. In the alternative, the storage medium may be integral to the processor. The processor and the storage medium may reside in a single ASIC or in discrete components in a computer system.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms comprises, comprising, or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A method comprising:
   receiving signals corresponding to a first parameter;
   performing an inversion of the received signals, including regularizing the inversion by a Duncan-Horn formulation of a Kalman filter, to generate a mapping of a second parameter; and
   providing the mapping to a user.

2. The method of claim 1, wherein the first parameter comprises electrocardial potentials at a distance from a surface of a heart, and wherein the second parameter comprises electrocardial potentials at the surface of the heart.

3. The method of claim 2, wherein the first parameter electrocardial potentials are measured at positions within a chamber of the heart.

4. The method of claim 2, wherein the first parameter electrocardial potentials are measured at positions external to the heart.

5. The method of claim 2, wherein the first parameter electrocardial potentials are measured simultaneously by a multi-electrode probe.

6. The method of claim 5, wherein the first parameter electrical potentials are measured simultaneously by regularly spaced electrodes on the multi-electrode probe.

7. The method of claim 2, wherein the first parameter electrocardial potentials are measured using a multi-sensor probe including elements selected from the group consisting of superconductive quantum interference devices, magnetometers and electrometer amplifier based sensors.

8. The method of claim 1, wherein the Duncan-Horn formulation of the Kalman filter is based upon multiple steps in time.

9. The method of claim 8, wherein the Duncan-Horn formulation of the Kalman filter is based upon a selectable number of steps in time.

10. The method of claim 1, wherein providing the mapping to a user comprises displaying a graphical image display of the mapping to the user.

11. A system comprising:
    a data processor;
    a data input interface coupled to the data processor; and
    a data output interface coupled to the data processor;
    wherein the processor is configured to
      receive input data corresponding to a first parameter from the data input interface,
      perform regularization using a Duncan-Horn formulation of a Kalman filter in generating output data corresponding to a second parameter, and
      provide the output data to the data output interface.

12. The system of claim 11, wherein the first parameter comprises electrocardial potentials at a distance from a surface of a heart, and wherein the second parameter comprises electrocardial potentials at the surface of the heart, and wherein the data processor is configured to generate a mapping of the electrocardial potentials at the surface of the heart.

13. The system of claim 12, further comprising a multi-electrode probe coupled to the data input interface and configured to measure the first parameter electrocardial potentials.

14. The system of claim 13, wherein the multi-electrode probe is configured to measure the first parameter electrocardial potentials at positions within a chamber of the heart.

15. The system of claim 13, wherein the multi-electrode probe is configured to measure the first parameter electrocardial potentials at positions external to the heart.

16. The system of claim 13, wherein the multi-electrode probe includes a plurality of regularly spaced electrodes.

17. The system of claim 12, further comprising a multi-sensor probe which includes elements selected from the group consisting of superconductive quantum interference devices, magnetometers and electrometer amplifier based sensors.

18. The system of claim 11, wherein the processor is configured to regularize the generation of the output data, wherein the Duncan-Horn formulation of the Kalman filter is based upon multiple steps in time.

19. The system of claim 18, wherein the processor is configured to regularize the generation of the output data, wherein the Duncan-Horn formulation of the Kalman filter is based upon a selectable number of steps in time.

20. The system of claim 11, wherein the data output interface comprises a graphical display, and wherein the processor is configured to provide the output data as a graphical mapping of the second parameter.

* * * * *